United States Patent
Na et al.

(10) Patent No.: US 9,063,059 B2
(45) Date of Patent: Jun. 23, 2015

(54) THREE-DIMENSIONAL MATRIX PHASED ARRAY SPOT WELD INSPECTION SYSTEM

(75) Inventors: Jeong K. Na, Centerville, OH (US); Roger Spencer, Ashville, OH (US); Paul C. Boulware, Columbus, OH (US)

(73) Assignee: EDISON WELDING INSTITUTE, INC., Columbus, OH (US)

( * ) Notice: Subject to any disclaimer, the term of this patent is extended or adjusted under 35 U.S.C. 154(b) by 605 days.

(21) Appl. No.: 13/468,502

(22) Filed: May 10, 2012

(65) Prior Publication Data

US 2012/0310551 A1    Dec. 6, 2012

Related U.S. Application Data

(60) Provisional application No. 61/484,312, filed on May 10, 2011.

(51) Int. Cl.
 *G01B 5/28* (2006.01)
 *G01N 29/06* (2006.01)
 *G01N 29/24* (2006.01)
 *G01N 29/26* (2006.01)
 *G01N 29/28* (2006.01)

(52) U.S. Cl.
 CPC ............ *G01N 29/0645* (2013.01); *G01N 29/24* (2013.01); *G01N 29/262* (2013.01); *G01N 29/28* (2013.01); *G01N 2291/106* (2013.01); *G01N 2291/2672* (2013.01)

(58) Field of Classification Search
 None
 See application file for complete search history.

(56) References Cited

U.S. PATENT DOCUMENTS

| | | |
|---|---|---|
| 3,895,685 A | 7/1975 | Gillette et al. |
| 3,978,714 A | 9/1976 | Shraiber et al. |

(Continued)

FOREIGN PATENT DOCUMENTS

| | | |
|---|---|---|
| WO | 2006071656 | 7/2006 |
| WO | 2007068979 | 6/2007 |

(Continued)

OTHER PUBLICATIONS

Dr. Michael D. C. Moles et al., Introduction to Phased Array Ultrasonic Technology Applications, 2004, pp. 6-18, R/D Tech, Inc., Canada.

(Continued)

*Primary Examiner* — Aditya Bhat
(74) *Attorney, Agent, or Firm* — McNees, Wallace & Nurick, LLC (57) ABSTRACT

A system for characterizing a spot weld including an acoustic probe that further includes a plurality of ultrasonic transducer elements arranged in a curved array, wherein the transducer elements are operative to generate ultrasonic signals and to receive reflections thereof; and a combination of materials for allowing the probe to conform to a contoured surface of the spot weld while enabling sound energy to be transferred directly into the spot weld under test conditions; a phased array excitation unit coupled to the array of transducer elements for ultrasonically exciting transducer elements; and a controller coupled to the phased array excitation unit for controlling the operation of the phased array unit, gathering and processing information from the ultrasonic transducers, and generating a two-dimensional, color coded image that characterizes the integrity of the spot weld.

17 Claims, 9 Drawing Sheets

(56) References Cited

U.S. PATENT DOCUMENTS

| | | | |
|---|---|---|---|
| 4,274,289 A | 6/1981 | Weiss et al. |
| 4,327,738 A | 5/1982 | Green et al. |
| 4,344,159 A | 8/1982 | Ballinger |
| 4,442,715 A | 4/1984 | Brisken et al. |
| 4,534,221 A | 8/1985 | Fife et al. |
| 4,631,710 A | 12/1986 | Yamaguchi et al. |
| 4,642,215 A | 2/1987 | Klinvex et al. |
| 4,744,250 A | 5/1988 | Ganglbauer et al. |
| 4,770,699 A | 9/1988 | Mountford |
| 4,836,026 A | 6/1989 | P'An et al. |
| 4,865,040 A | 9/1989 | Ogasawara |
| 4,886,069 A | 12/1989 | O'Donnell |
| 5,030,911 A | 7/1991 | Lam |
| 5,063,780 A | 11/1991 | Landry et al. |
| 5,121,364 A | 6/1992 | O'Donnell |
| 5,142,649 A | 8/1992 | O'Donnell |
| 5,278,757 A | 1/1994 | Hoctor et al. |
| 5,282,471 A | 2/1994 | Sato |
| 5,299,577 A | 4/1994 | Brown et al. |
| 5,331,964 A | 7/1994 | Trahey et al. |
| 5,351,543 A | 10/1994 | Migliori et al. |
| 5,473,943 A | 12/1995 | Schoenen et al. |
| 5,487,306 A | 1/1996 | Fortes |
| 5,513,532 A | 5/1996 | Beffy et al. |
| 5,531,117 A | 7/1996 | Fortes |
| 5,549,111 A | 8/1996 | Wright et al. |
| 5,677,490 A | 10/1997 | Gunther et al. |
| 5,750,895 A | 5/1998 | Chern et al. |
| 5,777,891 A | 7/1998 | Pagano et al. |
| 5,797,844 A | 8/1998 | Yoshioka et al. |
| 5,797,847 A | 8/1998 | Miller et al. |
| 6,055,862 A | 5/2000 | Martens |
| 6,072,144 A | 6/2000 | Perryman et al. |
| 6,250,163 B1 | 6/2001 | MacLauchlan et al. |
| 6,254,542 B1 | 7/2001 | Hamilton et al. |
| 6,279,397 B1 | 8/2001 | Dwyer |
| 6,332,011 B1 | 12/2001 | Johnson |
| 6,344,739 B1 | 2/2002 | Hardy et al. |
| 6,484,584 B2 | 11/2002 | Johnson et al. |
| 6,532,820 B1 | 3/2003 | Fleming et al. |
| 6,640,632 B1 | 11/2003 | Hatanaka et al. |
| 6,676,603 B2 | 1/2004 | Aichhorn et al. |
| 6,725,721 B2 | 4/2004 | Venczel |
| 6,732,587 B2 | 5/2004 | Lorraine et al. |
| 6,813,950 B2 | 11/2004 | Glascock et al. |
| 6,857,553 B1 | 2/2005 | Hartman et al. |
| 6,865,243 B2 | 3/2005 | Paillaman et al. |
| 6,911,008 B2 | 6/2005 | Pelissier et al. |
| 6,920,791 B2 | 7/2005 | Wagner et al. |
| 6,925,882 B1 | 8/2005 | Fleming et al. |
| 6,931,931 B2 | 8/2005 | Graff et al. |
| 6,945,937 B2 | 9/2005 | Culp et al. |
| 6,948,369 B2 | 9/2005 | Fleming et al. |
| 6,957,583 B2 | 10/2005 | Tooma et al. |
| 7,021,143 B2 | 4/2006 | Dasch |
| 7,132,617 B2 | 11/2006 | Lee et al. |
| 7,210,329 B2 | 5/2007 | Buschke et |
| 7,234,355 B2 | 6/2007 | Dewangan et al. |
| 7,240,556 B2 | 7/2007 | Georgeson et al. |
| 7,389,693 B2 | 6/2008 | Reed et al. |
| 7,428,842 B2 | 9/2008 | Fair et al. |
| 7,516,022 B2 | 4/2009 | Lee et al. |
| 7,650,790 B2 | 1/2010 | Wright |
| 7,694,566 B2 | 4/2010 | Kleinert |
| 7,698,944 B2 | 4/2010 | Takada |
| 7,735,369 B2 | 6/2010 | Young et al. |
| 7,757,557 B2 | 7/2010 | Thomas et al. |
| 7,779,693 B2 | 8/2010 | Orth et al. |
| 7,779,694 B2 | 8/2010 | Iizuka |
| 7,784,347 B2 | 8/2010 | Messer et al. |
| 7,784,348 B2 | 8/2010 | Dubois et al. |
| 7,789,286 B2 | 9/2010 | Maev et al. |
| 7,926,349 B2 | 4/2011 | Sargent |
| 7,984,651 B2 | 7/2011 | Randall et al. |
| 8,076,824 B2 | 12/2011 | Sawada et al. |
| 8,079,263 B2 | 12/2011 | Randall et al. |
| 8,164,982 B2 | 4/2012 | Okuda et al. |
| 8,166,822 B1 | 5/2012 | Urbano et al. |
| 8,220,334 B2 | 7/2012 | Klessel et al. |
| 8,365,584 B1 | 2/2013 | Quinones et al. |
| 8,485,036 B2 | 7/2013 | Crumpton et al. |
| 8,499,634 B2 | 8/2013 | Urbano et al. |
| 8,499,635 B2 | 8/2013 | Klessel et al. |
| 8,521,446 B2 | 8/2013 | Zhang et al. |
| 8,544,714 B1 | 10/2013 | Obaditch et al. |
| 8,554,328 B2 | 10/2013 | Faraji et al. |
| 8,600,299 B2 | 12/2013 | Randall et al. |
| 8,616,062 B2 | 12/2013 | Kono et al. |
| 8,649,185 B2 | 2/2014 | Wodnicki et al. |
| 8,656,783 B2 | 2/2014 | Randall et al. |
| 8,689,850 B2 | 4/2014 | Hull |
| 8,695,429 B2 | 4/2014 | Urbano et al. |
| 8,746,070 B2 | 6/2014 | Tippit, Jr. et al. |
| 2004/0020298 A1* | 2/2004 | Siverling et al. ............... 73/644 |
| 2005/0132809 A1* | 6/2005 | Fleming et al. ............... 73/597 |
| 2008/0114253 A1 | 5/2008 | Randall et al. |
| 2008/0196504 A1* | 8/2008 | Johnson et al. ............... 73/588 |
| 2009/0007678 A1 | 1/2009 | Fukutomi et al. |
| 2009/0133501 A1* | 5/2009 | Georgeson ............... 73/632 |
| 2009/0255341 A1 | 10/2009 | Zimmerman et al. |
| 2009/0320598 A1 | 12/2009 | Puchner et al. |
| 2010/0224000 A1 | 9/2010 | Komatsu et al. |
| 2010/0286527 A1 | 11/2010 | Cannon et al. |
| 2011/0120223 A1 | 5/2011 | MacLauchlan et al. |
| 2012/0034044 A1 | 2/2012 | Sloan |
| 2012/0065937 A1 | 3/2012 | de Graff et al. |
| 2012/0091185 A1 | 4/2012 | Ume et al. |
| 2012/0167690 A1 | 7/2012 | Yamano |
| 2012/0243771 A1 | 9/2012 | Matsumoto et al. |
| 2012/0272739 A1 | 11/2012 | Both et al. |
| 2013/0167646 A1 | 7/2013 | Frederick et al. |
| 2013/0181574 A1 | 7/2013 | Chaggares et al. |
| 2013/0194891 A1 | 8/2013 | Kristoffersen et al. |
| 2013/0228560 A1 | 9/2013 | Ume et al. |
| 2013/0255384 A1 | 10/2013 | Putshery et al. |
| 2013/0308419 A1 | 11/2013 | Singh et al. |
| 2013/0312528 A1 | 11/2013 | Feydo |
| 2013/0315035 A1 | 11/2013 | Tai |
| 2013/0319120 A1 | 12/2013 | Fetzer et al. |
| 2013/0338941 A1 | 12/2013 | Lin et al. |
| 2014/0107534 A1 | 4/2014 | Du et al. |

FOREIGN PATENT DOCUMENTS

| | | |
|---|---|---|
| WO | 2010097269 | 9/2010 |
| WO | 2012058473 A1 | 5/2012 |
| WO | 2012103628 A1 | 8/2012 |
| WO | 2012167380 A1 | 12/2012 |
| WO | 2013044350 A1 | 4/2013 |
| WO | 2014062467 A1 | 4/2014 |
| WO | 2014081721 A1 | 5/2014 |
| WO | 2014100217 A1 | 6/2014 |

OTHER PUBLICATIONS

Moles et al., "Pipeline Girth Weld Inspections using Ultrasonic Phased Arrays," Pan-American Conference for Nondestructive Testing, Rio De Janeiro, Brazil, Jun. 6, 2003, entire document.

International Search Report and Written Opinion received in PCT/US2009/049428, mailed Aug. 31, 2009.

International Search Report and Written Opinion received in PCT/US2012/037322, mailed Aug. 27, 2012.

* cited by examiner

THE ARROWS IN THE DIAGRAM REPRESENT HOW A SOUND WAVE TRANSMITS AND REFLECTS AT A MATERIAL'S INTERFACE. A THINNER LINE REPRESENTS LOSS OF ACOUSTIC ENERGY AS THE SOUND WAVE INTERACTS WITH A SURFACE

3-Dimensional Array Element

FIG. 6A

Red Elements: 0 delay
  Blue Elements: (n) nano-second delay
  Green Element: (n+m) nano-second delay continues till 8th group

THREE-DIMENSIONAL MATRIX PHASED ARRAY SPOT WELD INSPECTION SYSTEM

CROSS-REFERENCE TO RELATED APPLICATIONS

This patent application claims the benefit of U.S. Provisional Patent Application Ser. No. 61/484,312 filed on May 10, 2011 and entitled "Three-Dimensional Matrix Phased Array Spot Weld Inspection System", the disclosure of which is hereby incorporated by reference herein in its entirety and made part of the present U.S. utility patent application for all purposes.

BACKGROUND OF THE INVENTION

The present invention relates generally to inspection systems for use in assessing the performance of industrial manufacturing processes, and more specifically to a nondestructive inspection system for assessing the quality of resistance spot welds.

Sheet metal joining processes are widely used in many industries including the aerospace and automotive industries. Among these processes, resistance spot welding is a very common procedure used to join metal sheets because it has high process speed and is easily adopted in mass production lines. Seam welding, weld bonding, adhesive joining, soldering, and brazing have also gained acceptance. The quality control of such joining processes has been recognized as an important issue to manufacturers. The quality of weld joints is affected by the joining process itself and by the design of the joint. Many factors are considered, including metallurgic reactions, thermal behaviors, chemical composition, starting condition of the base metal, welding and bonding conditions, and the welding and bonding equipment used during the process. Furthermore, the intricate relationship between these factors makes it difficult to control the quality of the weld joint and difficult to inspect the weld joint in a nondestructive manner.

Acoustic methods are commonly used nondestructive testing methods for various inspection applications. Unlike other nondestructive testing methods, acoustic methods provide both surface and internal information. Moreover, acoustic methods allow for deeper penetration into specimens and higher sensitivity to small discontinuities in a weld joint. Acoustic methods, however, do have limitations. The most significant limitations include the requirement of a skillful operator for using the testing device and analyzing acoustic data, as well as the very subjective nature of identifying a stuck or cold weld or inadequate bond, such as a kissing bond. Accordingly, the field of ultrasonic nondestructive evaluation (NDE) is in need of a reliable process or technique for identifying poor quality joints in a manner that eliminates the involvement of a skilled operator and the subjective interpretation of test data.

SUMMARY OF THE INVENTION

The following provides a summary of certain exemplary embodiments of the present invention. This summary is not an extensive overview and is not intended to identify key or critical aspects or elements of the present invention or to delineate its scope.

In accordance with one aspect of the present invention, a system for characterizing a spot weld is provided. This system includes an acoustic probe having a plurality of ultrasonic transducer elements arranged in a curved array at one end of the acoustic probe, wherein the transducer elements are operative to both generate ultrasonic signals and to receive reflections thereof; and a combination of materials for allowing the probe to conform to a contoured surface of the spot weld while enabling sound energy to be transferred directly into the spot weld under test conditions. The system also includes a phased array excitation unit in electrical communication with the array of transducer elements for ultrasonically exciting transducer elements; and a controller in electrical communication with the phased array excitation unit for controlling the operation of the phased array unit, gathering and processing information from the ultrasonic transducers, and generating a two-dimensional, color coded image that characterizes the integrity of the spot weld.

In accordance with another aspect of the present invention, a non-destructive test system for characterizing a spot weld is provided. This system includes an acoustic probe, having a plurality of ultrasonic transducer elements arranged in a curved array at one end of the acoustic probe, wherein the transducer elements are operative to both generate ultrasonic signals and to receive reflections thereof; and a combination of materials for allowing the probe to conform to a contoured surface of the spot weld while enabling sound energy to be transferred directly into the spot weld under test conditions, wherein the combination of materials further includes a flexible membrane mounted on the end of the probe and a fluid filled chamber or solid sound delay material disposed between the membrane and the array. The system also includes a phased array excitation unit in electrical communication with the array of transducer elements for ultrasonically exciting the transducer elements; and a computerized controller in electrical communication with the phased array excitation unit for controlling the operation of the phased array unit, gathering and processing information from the ultrasonic transducers, and generating a two-dimensional, color coded image that characterizes the integrity of the spot weld.

In yet another aspect of this invention, an alternate a non-destructive test system for characterizing a spot weld is provided. This system includes an acoustic probe having a plurality of ultrasonic transducer elements arranged in a curved array at one end of the acoustic probe, wherein the transducer elements are operative to both generate ultrasonic signals and to receive reflections thereof, wherein the transducer elements are further arranged into discrete subgroups, and wherein each subgroup may be activated independently of the other subgroups; and a combination of materials for allowing the probe to conform to a contoured surface of the spot weld while enabling sound energy to be transferred directly into the spot weld under test conditions, wherein the combination of materials further includes a flexible membrane mounted on the end of the probe and a fluid filled chamber or solid sound delay material disposed between the membrane and the array. The system also includes a phased array excitation unit in electrical communication with the array of transducer elements for ultrasonically exciting the transducer elements; and a computerized controller in electrical communication with the phased array excitation unit for controlling the operation of the phased array unit, gathering and processing information from the ultrasonic transducers, and generating a two-dimensional, color coded image that characterizes the integrity of the spot weld.

Additional features and aspects of the present invention will become apparent to those of ordinary skill in the art upon reading and understanding the following detailed description of the exemplary embodiments. As will be appreciated by the skilled artisan, further embodiments of the invention are possible without departing from the scope and spirit of the invention. Accordingly, the drawings and associated descriptions are to be regarded as illustrative and not restrictive in nature.

BRIEF DESCRIPTION OF THE DRAWINGS

The accompanying drawings, which are incorporated into and form a part of the specification, schematically illustrate one or more exemplary embodiments of the invention and, together with the general description given above and detailed description given below, serve to explain the principles of the invention, and wherein.

DETAILED DESCRIPTION OF THE INVENTION

Exemplary embodiments of the present invention are now described with reference to the Figures. Reference numerals are used throughout the detailed description to refer to the various elements and structures. In other instances, well-known structures and devices are shown in block diagram form for purposes of simplifying the description. Although the following detailed description contains many specifics for the purposes of illustration, a person of ordinary skill in the art will appreciate that many variations and alterations to the following details are within the scope of the invention. Accordingly, the following embodiments of the invention are set forth without any loss of generality to, and without imposing limitations upon, the claimed invention.

The present application incorporates by reference herein U.S. patent application Ser. No. 12/186,047, in its entirety for all purposes. With regard to the nomenclature used herein, the present invention is described as being useful for analyzing the integrity of a resistance spot weld between a first and second workpiece or upper and lower sheets of metal. However, this invention is applicable to all welds regardless of material, configuration, or the number of workpieces, as well as adhesive bonds. Thus, while the present disclosure generally refers to a stuck weld, one skilled in the art will appreciate that the present invention detects stuck portions of joints, which are often referred to as kissing bonds or weak bonds in the field of adhesives. This invention is also applicable to metals and nonmetals alike and is not limited to fusion welding, but may also be used to examine solid state welds, brazed and soldered joints. Thus, while this method has particular application in the automated analysis of spot welds, it may also be used to evaluate continuous bonds.

A stuck weld or stuck joint occurs when workpieces (e.g., pieces of sheet metal) are held together by localized fusion at the welding interface, but no weld button or weld nugget has formed as a result of the welding process. A stuck weld typically results from heat at the welding interface being insufficient to create nugget growth. In the absence of a properly formed weld nugget, fusion may occur at certain points of contact between the sheets of metal. With coated materials, coatings can melt and refreeze, effectively soldering the parts together. The resulting bonds are often strong enough to hold the workpieces together under light loads, but reasonable force will pull them apart. If ultrasonic testing is used to analyze weld integrity, transmitted ultrasonic beams (i.e., sound waves) will not pass through the interface between sheets if no fusion has occurred. If a stuck weld as occurred, resulting in fusion, but no weld nugget, transmitted ultrasonic beams will pass partially though the sheet interface. If a weld nugget has been properly formed, transmitted ultrasonic beams will pass completely through the sheet interface.

Phased Array Ultrasonic Testing (PAUT) may be used for flaw detection, sizing, and imaging. PAUT technology is the ability to modify electronically the acoustic probe characteristics. Probe modifications are performed by introducing time shifts in the signals sent to (pulse) and received from (echo) individual elements of an array probe. Three common formats for collecting and displaying ultrasonic data for purposes of non-destructive evaluation are A-scan, B-scan and C-scan presentations. Each presentation mode provides a means for visualizing and evaluating the region of material being inspected. An A-scan is a simple RF waveform presentation showing the time and amplitude of an ultrasonic signal, as commonly provided by conventional ultrasonic flaw detectors and waveform display thickness gages. A-scan is an amplitude modulation scan, and as generally applied to pulse echo ultrasonics, horizontal and vertical sweeps are proportional to time or distance and amplitude or magnitude respectively. Thus the location and magnitude of acoustical interface are indicated as to depth below the transducer. The relative amount of energy received is plotted along the vertical axis and the elapsed time (which may be related to the sound energy travel time within the material) is displayed along the horizontal axis. Most instruments utilizing an A-scan display allow the signal to be displayed in its natural radio frequency form (RF) as a fully rectified RF signal or as either the positive or negative half of the RF signal. In the A-scan presentation, relative discontinuity size can be estimated by comparing the signal amplitude obtained from an unknown reflector to that from a known reflector. Reflector depth can be determined by the position of the signal on the horizontal sweep. A C-scan from a phased array system involves an ultrasonic probe being physically moved along one axis while the beam electronically scans along the other axis according to the focal law sequence. Signal amplitude or depth data is collected within gated regions of interest. Data is plotted with each focal law progression, using the programmed beam aperture. Utilizing a matrix phased array probe, beam steering can be accomplished in multiple directions.

Figure 1:
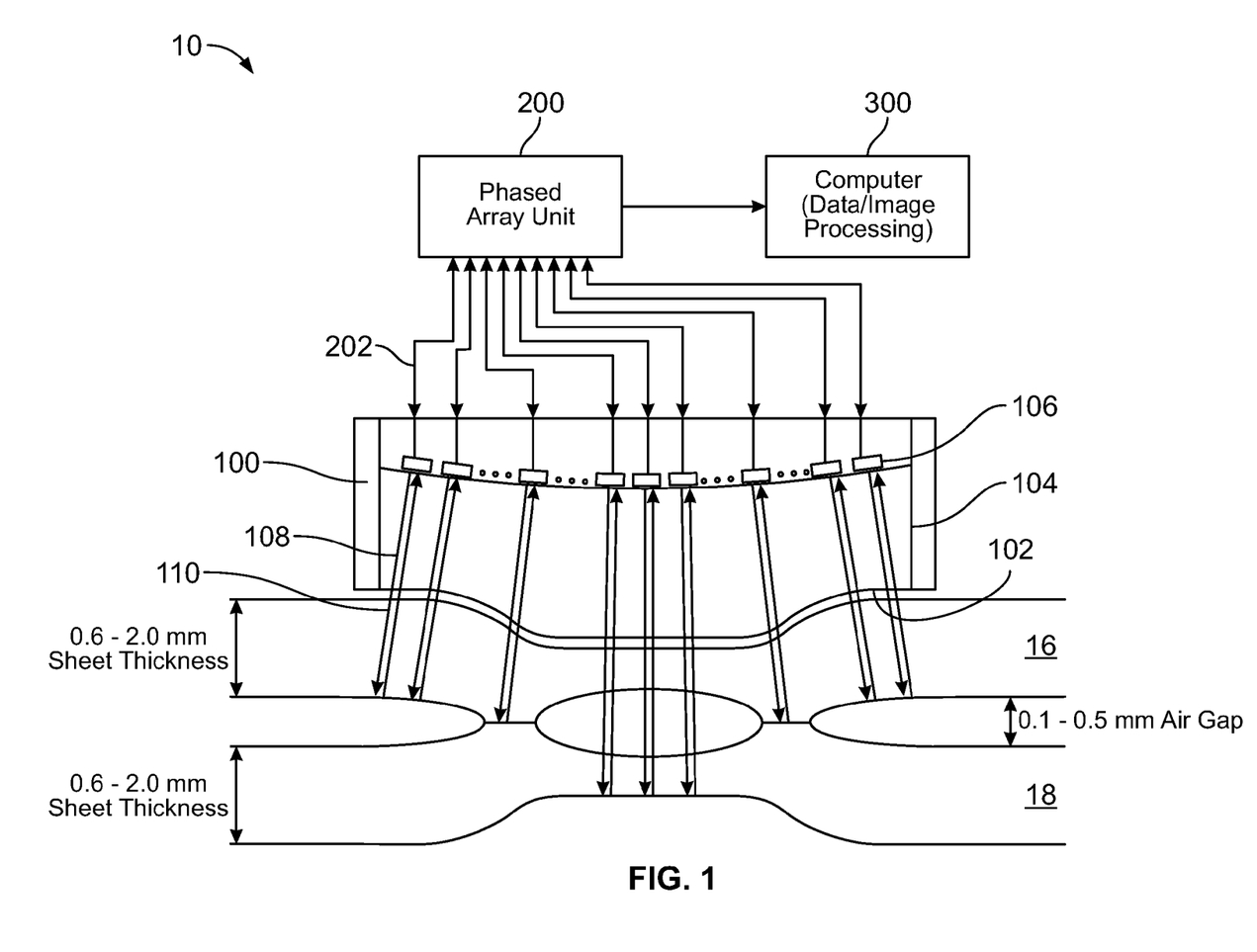
FIG. 1 is a block diagram showing the primary components of a three-dimensional matrix phased array spot weld inspection system in accordance with an exemplary embodiment of the present invention.

With reference to the Figures, an exemplary embodiment of the present invention provides a nondestructive inspection system for assessing the quality of resistance spot welds. As shown in FIG. 1, which is a block diagram of an exemplary embodiment, spot weld inspection system 10, is operative to assess the quality of weld 12, which is formed at interface 14, which is located between upper sheet 16 and lower sheet 18

(both having a sheet thickness of about 0.6 mm to about 2.0 mm). An air gap of about 0.1 mm to about 0.5 mm may be present between upper sheet 16 and lower sheet 18. A three-dimensional, matrix phased array probe 100 is placed on the region of upper sheet 16 that is located over the welded area. A curved array of ultrasonic elements 106 is used to transmit a plurality of ultrasonic beams 108 into the welded area and to capture the associated reflections 110 of those ultrasonic beams. Phased array unit 200 is in electrical communication with the plurality of ultrasonic elements 102 through a plurality of signal pathways 202. Phased array unit 200 is also in electrical communication with computer 300, which processes incoming ultrasonic data and generates a visual representation of the welded area. Probe 100 includes flexible membrane 102, which allows the tip of the probe to conform to the contour of the welded area and fluid filled chamber 104 or solid sound delay material for focusing and steering ultrasonic beams 108. Because flexible membrane 102 is capable of conforming to curved surfaces as shown in FIG. 1, and because the array of transducer elements 106 is configured in a curved geometry (see FIG. 1), the matrix phased array system of this invention is referred to as "three-dimensional" as opposed a "two-dimensional" system which uses a probe having a flattened array and a flat tip.

Figure 2A:
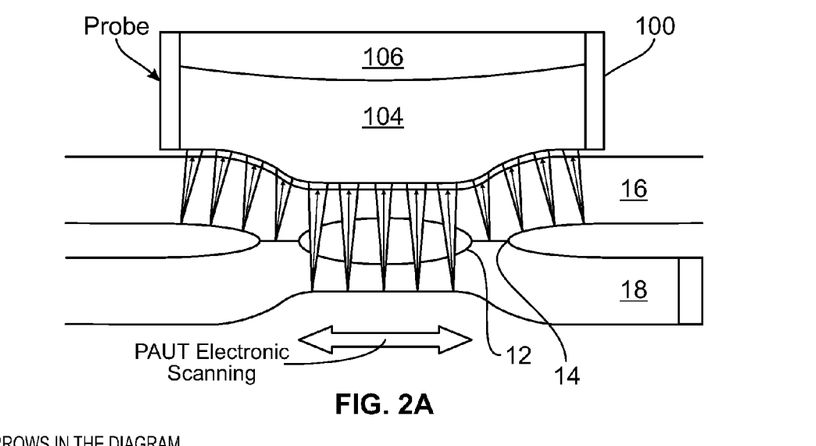
FIGS. 2a-c provide illustrations of test results derived from analyzing a good spot weld using the system of FIG. 1.
Figure 2B:
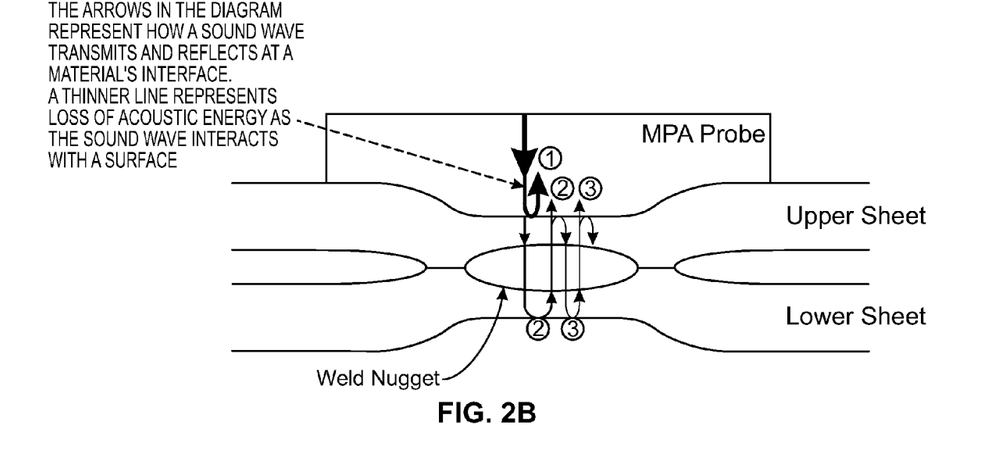
Figure 2C:
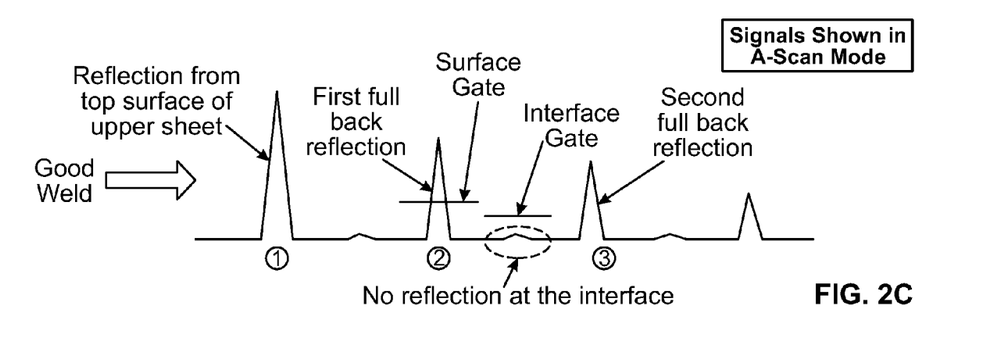
Figure 3:
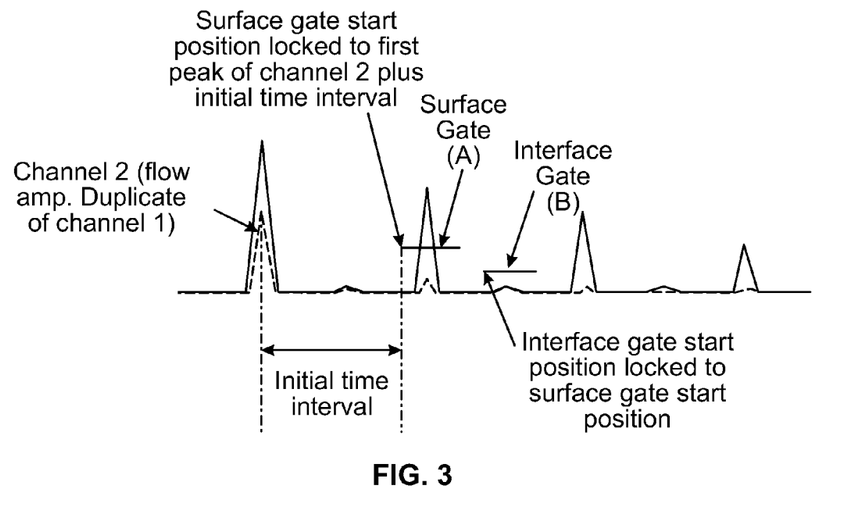
FIG. 3 provides a visual representation in A-scan mode of the electronic gates included in the weld inspection system of FIG. 1.

FIGS. 2a-c provide illustrations of test results derived from analyzing a good spot weld using system 10. In FIG. 2a, ultrasonic beams travel completely through weld 12 and interface 14 and reflect back to probe 100 from the backside of lower sheet 18. FIG. 2b illustrates diagrammatically the direction and relative strength of each sound wave as it transmits and reflects at interface 14. In FIG. 2b, a thinner line represents loss of acoustic energy as the sound wave interacts with interface 14. The reflected signals designated as circled 1, 2, and 3 correspond to the peaks shown in the A-scan presented in FIG. 2c. FIG. 2c provides the signals derived from testing in A-scan mode, wherein signal 1 represents the reflection from the top surface of upper sheet 16, signal 2 represents the first full back reflection, and signal 3 represents the second full back reflection. The horizontal line drawn through signal 2 represents a surface gate and the horizontal line adjacent to signal 2 represents an interface gate (see discussion below.)

Based on the ultrasonic energy transmission and reflection at weld interface 14 and the back side of lower sheet 18, system 10 uses two adjustable electronic gates to filter out all unwanted reflected signals. The two signals that pass through the gates are either the reflected signal from the back side of the second sheet of metal or the reflected signal from the interface of the two sheet metals. The first gate is called the "surface gate" and the second gate is called the "interface gate". This approach differs from the current commercially available systems that utilize an attenuation coefficient compensation method. In such systems, multiple reflections from all of surfaces and the interface are taken into account to determine attenuation coefficients and make a correction for acoustic energy loss caused by the spot weld fusion, assuming that the microstructure of fused section of the spot weld has a higher attenuation coefficient compared to a stuck weld condition. As disclosed and claimed in U.S. patent application Ser. No. 12/186,047, which is incorporated by reference herein, each ultrasonic element in array 106 generates a primary ultrasonic beam and a secondary ultrasonic beam wherein the primary ultrasonic beam is high gain and wherein the secondary ultrasonic beam is low gain; and wherein the primary and secondary ultrasonic beams are fired in within very close proximity to one another (i.e., milliseconds). As shown in FIG. 4, channel 2 is a low amplitude duplicate of channel 1 in each peak. The initial time interval shown is measured from the center of the first peak to the surface gate start position. The surface gate start position is locked to the first peak of channel 2 plus the initial time interval. The interface gate start position is locked to the surface gate start position. System 10 measures the ration of signal amplitude (height) between gate A and B and only signals between the gate start and end positions are considered.

Figure 4A:
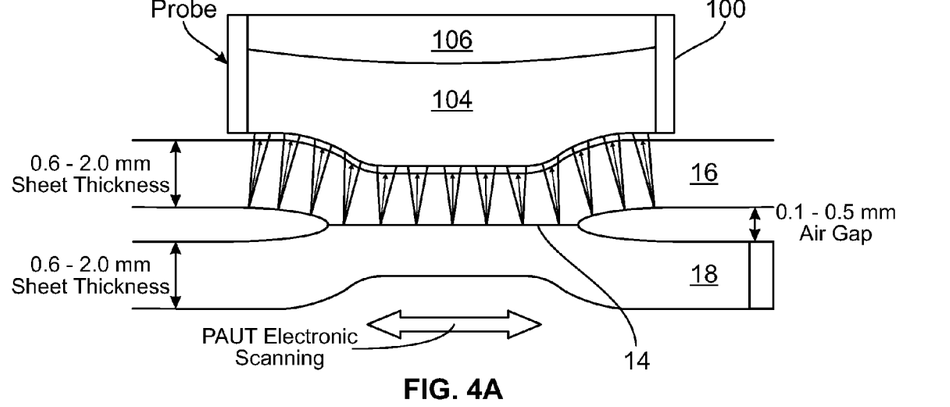
FIGS. 4a-c provide illustrations of test results derived from analyzing a poor spot weld using the system of FIG. 1.
Figure 4B:
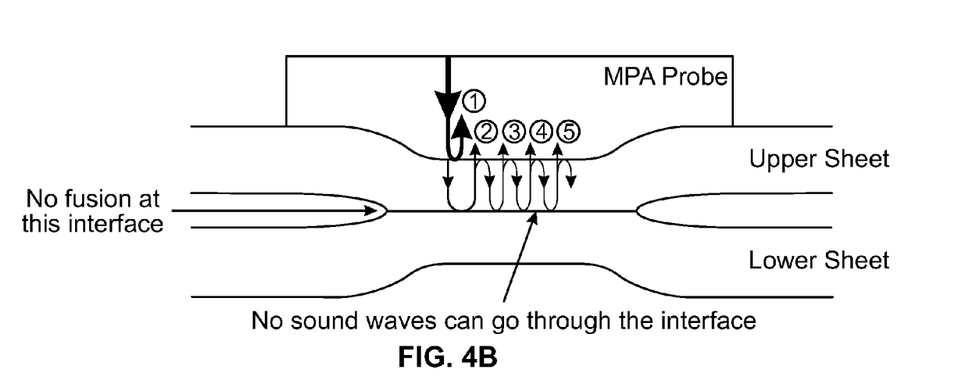
Figure 4C:
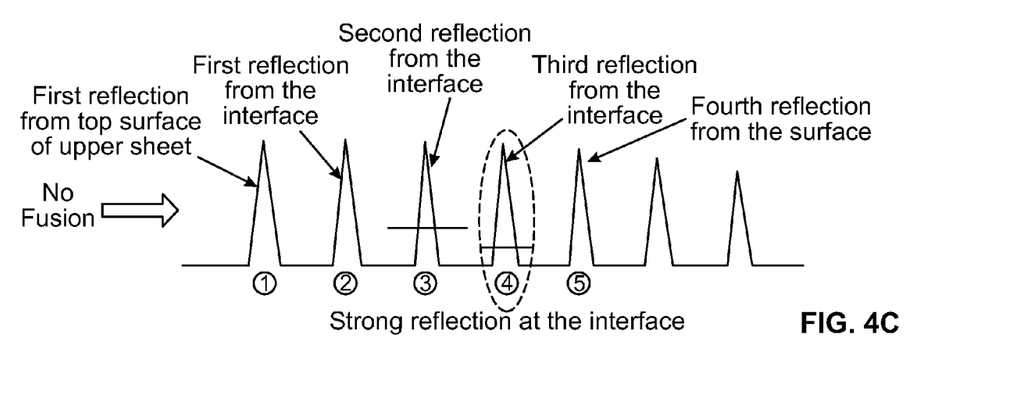

FIGS. 4a-c provide illustrations of test results derived from analyzing a poor spot weld using system 10. In FIG. 4a, because no weld nugget exists, ultrasonic beams do not travel completely through interface 14, but rather reflect back to probe 100 from interface 14. FIG. 4b illustrates diagrammatically the direction and relative strength of each sound wave as it reflects at interface 14. In FIG. 4b, a thinner line represents loss of acoustic energy as the sound wave interacts with interface 14. The reflected signals designated as circled 1, 2, 3, 4, and 5 correspond to the peaks shown in the A-scan presented in FIG. 4c. FIG. 4c provides the signals derived from testing in A-scan mode, wherein signal 1 represents the first reflection from the top surface of upper sheet 16, signal 2 represents the first reflection from interface 14, signal 3 represents the second reflection from interface 14, signal 4 represents the third reflection from interface 14, and signal 5 represents the fourth reflection from interface 14. The horizontal line drawn through signal 3 represents the surface gate and the horizontal line drawn though signal 4 represents the interface gate (see discussion above.)

Figure 5A:
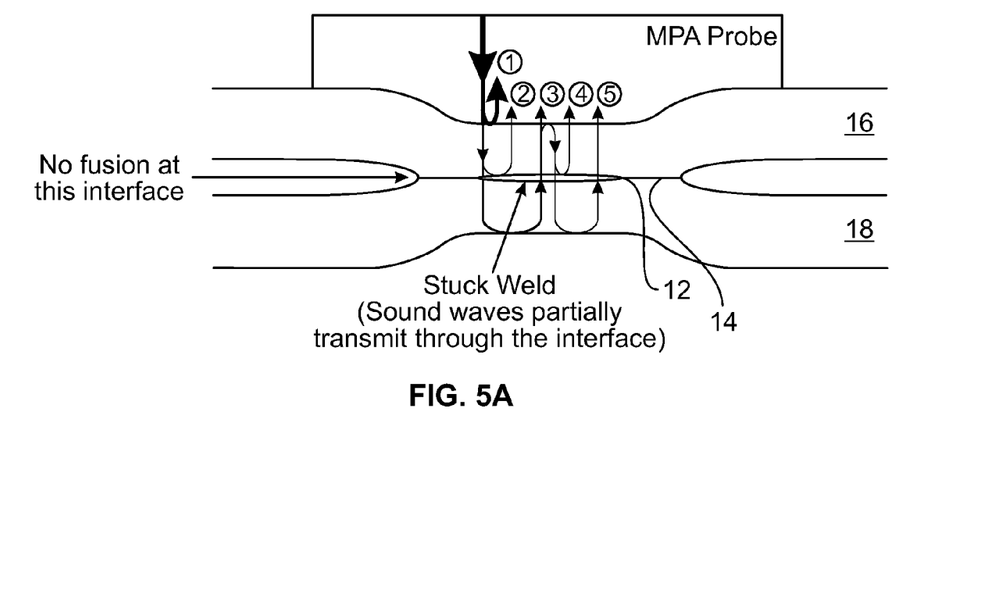
FIGS. 5a-b provide illustrations of test results derived from analyzing a stuck weld using the system of FIG. 1.
Figure 5B:
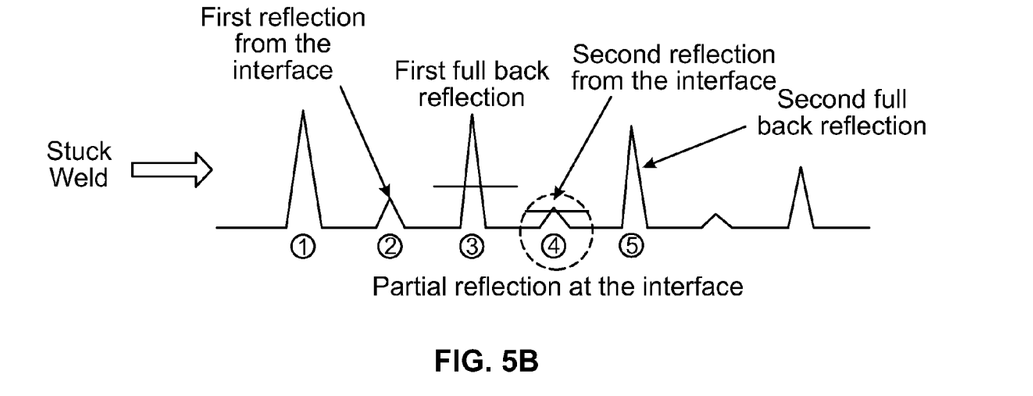

FIGS. 5a-b provide illustrations of test results derived from analyzing a stuck weld using system 10. Because an incomplete or poorly formed weld exists, ultrasonic beams travel only partially through interface 14, while intermediate echoes appear between the echoes of interface 14 and full back wall reflection. FIG. 5a illustrates diagrammatically the direction and relative strength of each sound wave as it transmits and reflects at interface 14. In FIG. 5a, a thinner line represents loss of acoustic energy as the sound wave interacts with interface 14. The reflected signals designated as circled 1, 2, 3, 4, and 5 correspond to the peaks shown in the A-scan presented in FIG. 5b. FIG. 5b provides the signals derived from testing in A-scan mode, wherein signal 2 represents the first reflection from interface 14, signal 3 represents the first full back reflection, signal 4 represents the second reflection from interface 14, and signal 5 represents the second full back reflection. The horizontal line drawn through signal 3 represents the surface gate and the horizontal line drawn though signal 4 represents the interface gate (see discussion above.)

Figure 6A:
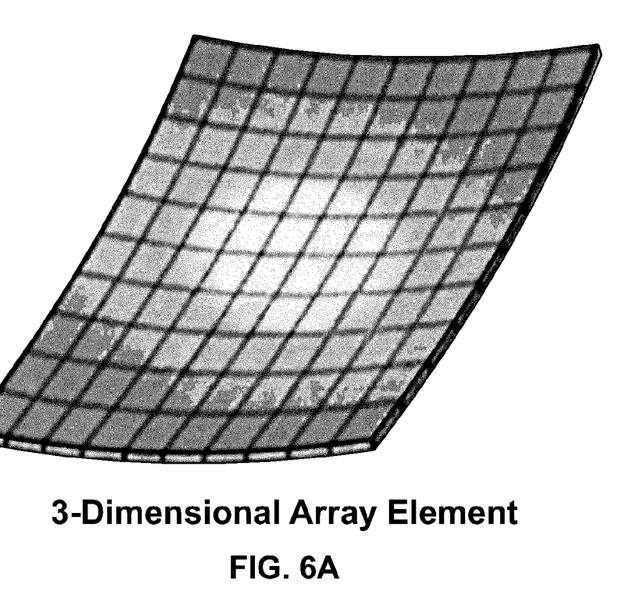
FIGS. 6a-b illustrate the shape of the 3-D curved probe element as well as various firing sequences for the sub-element groups.
Figure 6B:
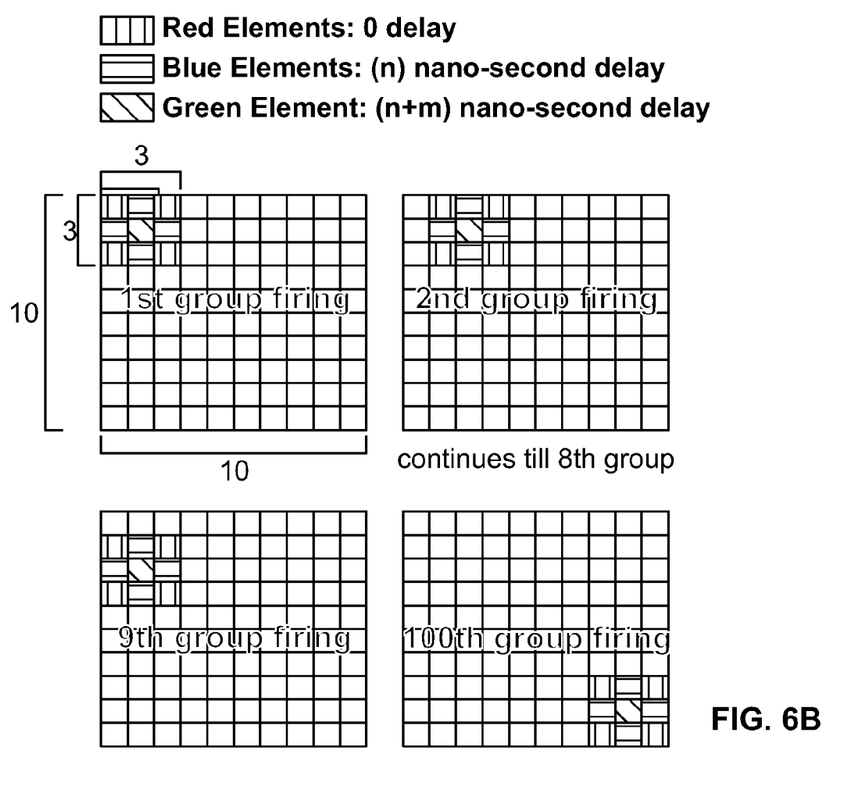

FIGS. 6a-b illustrate the geometry of the curved three-dimensional probe element (FIG. 6a) as well as various firing sequences for the sub-element groups (FIG. 6b). Acoustic probe 100 includes a plurality of ultrasonic transducer elements 106 arranged in a three-dimensional array and having a combination of materials for allowing the probe to conform to the contoured surface of a spot weld while enabling the sound energy to be transferred directly into the spot weld under test. An excitation element (phased array unit 200) is coupled to the array and a subset group of transducer elements are combined to send an ultrasonic beam toward a spot weld. Each transducer element in a subset group may be pulsed at different time intervals (phase delay) and their individual waves summed to produce a focusing effect of the beam as well as a steering effect. Other three-dimensional arrangements are possible for optimizing the performance for specific applications. The total number of elements, overall dimension, and operating frequency determine the overall three-dimensional surface contour shape and its operating characteristics and parameters.

Figure 7A:
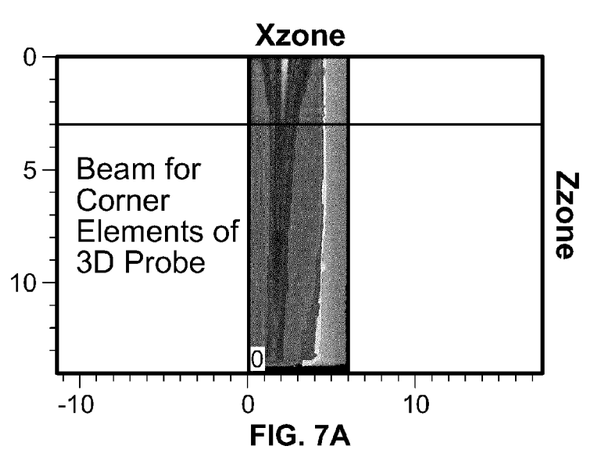
FIGS. 7a-d provide modeling verification of the benefits of a 3-D curved probe design versus a 2-D flat probe design.
Figure 7B:
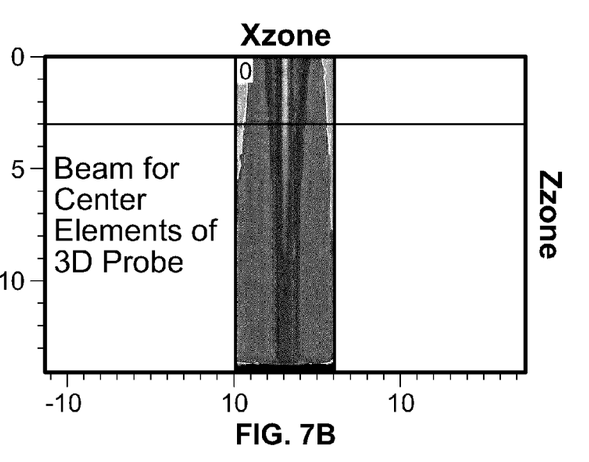
Figure 7C:
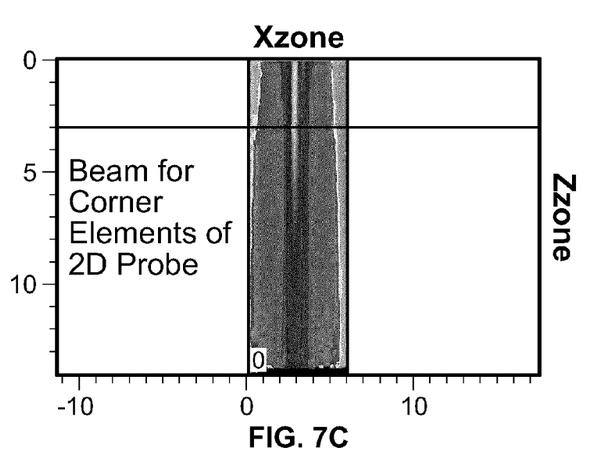
Figure 7D:
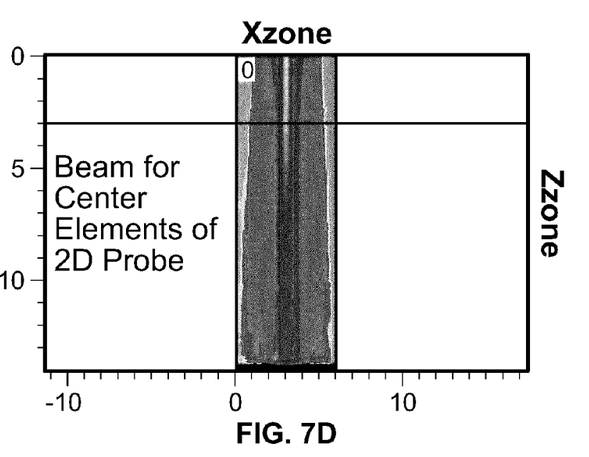

The design of the three-dimensional probe permits inspection of a larger physical area with a smaller probe, thereby allowing for improved probe access as well as a wider coverage area compared to two-dimensional designs. The three-dimensional geometrical arrangement provides optimized accuracy and sensitivity in particular regions of the weld joint. As illustrated by FIGS. 7a-d, the result of corner elements of the three-dimensional curved probe shown in FIG. 7a illustrates that the beam launch angle is more steered to the normal direction of the typical spot weld indentation when compared to the two-dimensional flat probe case shown in FIG. 7c. There is no noticeable change in the beam quality for the center elements for both three-dimensional (FIG. 7b) and two-dimensional (FIG. 7d) probes. Without losing the high fidelity of inspection capability with the two-dimensional matrix phased array probe, the three-dimensional probe extends the coverage area from the built-in curvature of the probe itself. This invention therefore allows inspection of a larger weld area with a smaller probe diameter, allowing improved access. It may also allow use of fewer numbers of elements, reducing overall system cost, while still covering the entire weld area.

Figure 8:
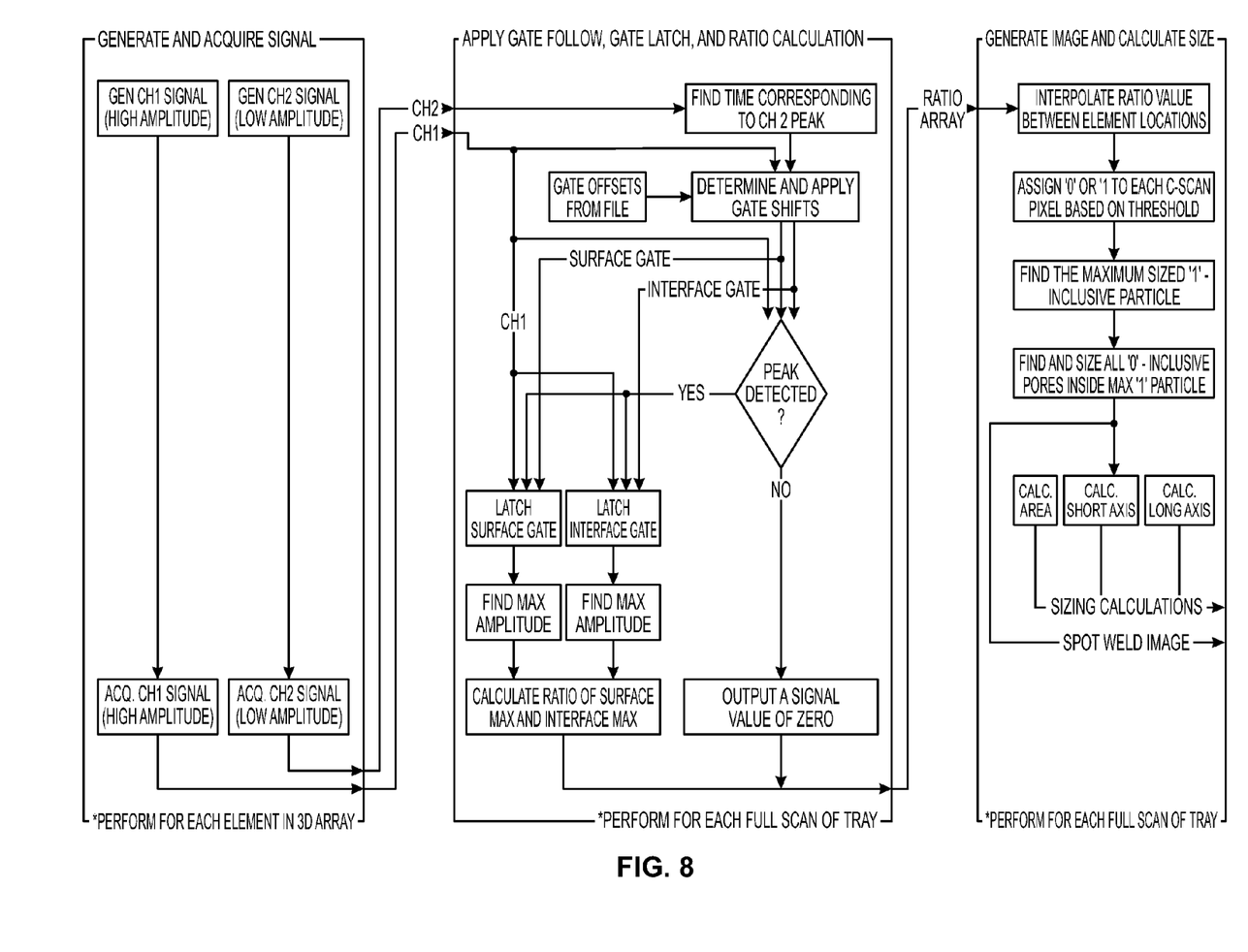
FIG. 8 provides a data flow chart for an exemplary embodiment of the spot weld inspection process of the present invention.
Figure 9:
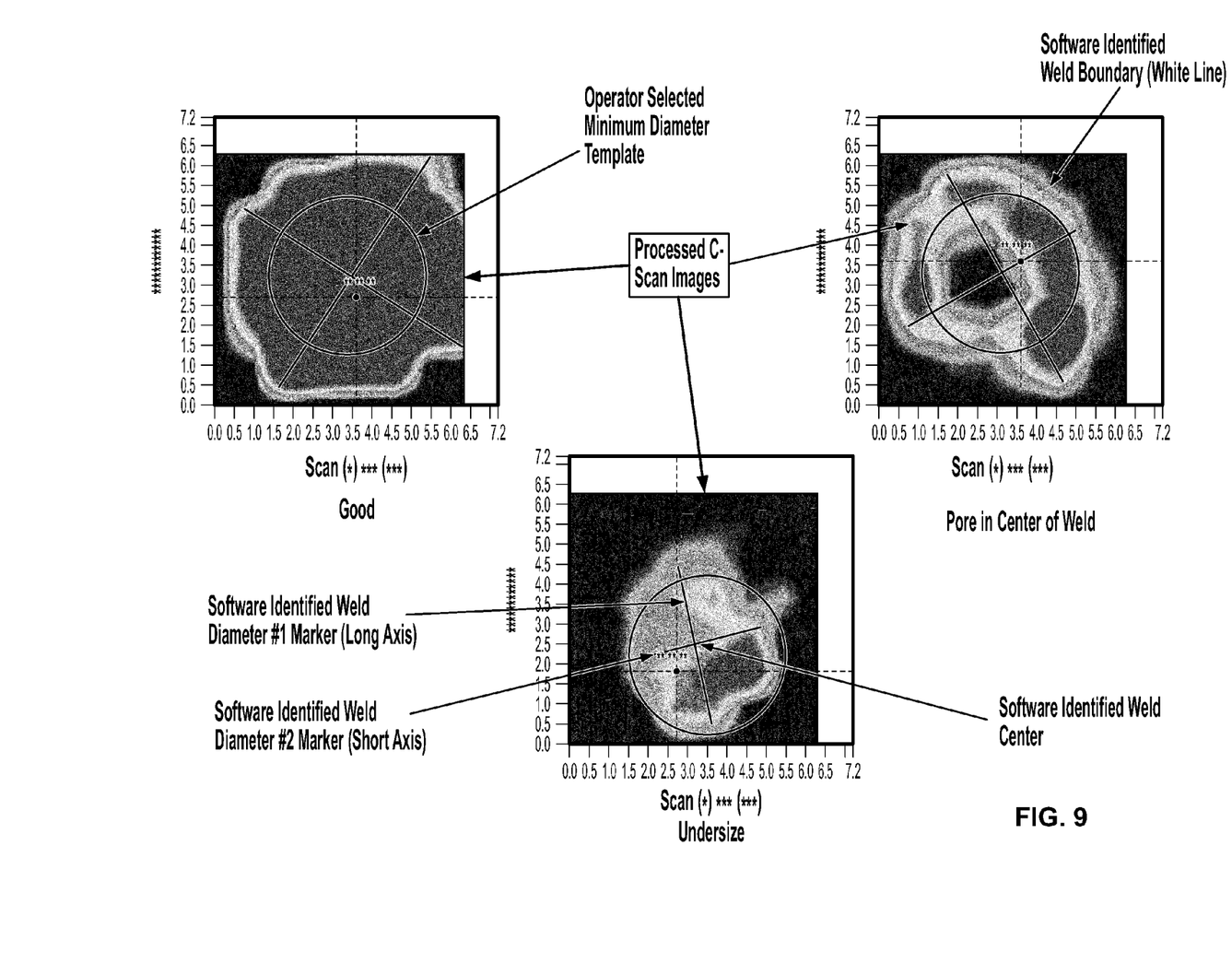
FIG. 9 provides examples of imaging results for various spot weld conditions.

In various embodiments of this invention, a computerized controller is coupled to acoustic probe 100 and transducer elements 106 for directing transmission of the ultrasonic signals and for summing and receiving responses therefrom. With general reference to FIG. 8 (which provides a flowchart that illustrates the function of one possible operating system), the controller is operative to (i) generate and acquire acoustic signals; (ii) detect the surface of the spot weld for each element grouping; (iii) adjust instrument gating to compensate for surface profile and differences in probe orientation; (iv) measure the signal amplitude ratio between responses reflected from the un-bonded areas and areas with good bond; (v) recognize a subset of the responses as being reflected from the un-bonded areas associated with the spot weld and to separate the subset from a remainder of the responses; (vi) measure the extent of the non-delamination dimensions; and (vii) present a two-dimensional color coded image of non-delamination of the spot weld (see FIG. 9).

In summary, some of the distinct advantages of this invention include: (i) a three-dimensional matrix probe element; (ii) a phase delay with sub-element group to form a beam focusing and steering capability; (iii) conformable membrane (no need for an attenuation correction); and (iv) an image process utilizing electronic gates to filter out unwanted reflections. While the present invention has been illustrated by the description of exemplary embodiments thereof, and while the embodiments have been described in certain detail, it is not the intention of the Applicant to restrict or in any way limit the scope of the appended claims to such detail. Additional advantages and modifications will readily appear to those skilled in the art. Therefore, the invention in its broader aspects is not limited to any of the specific details, representative devices and methods, and/or illustrative examples shown and described. Accordingly, departures may be made from such details without departing from the spirit or scope of the applicant's general inventive concept.

What is claimed:

1. A system for characterizing a spot weld, comprising:
   (a) an acoustic probe, wherein the acoustic probe further includes:
      (i) a plurality of ultrasonic transducer elements arranged in a curved array at one end of the acoustic probe, wherein the transducer elements are operative to both generate ultrasonic signals and to receive reflections thereof; and
      (ii) a combination of materials for allowing the probe to conform to a contoured surface of the spot weld while enabling sound energy to be transferred directly into the spot weld under test conditions,
   (b) a phased array excitation unit in electrical communication with the array of transducer elements for ultrasonically exciting transducer elements, and
   (c) a controller in electrical communication with the phased array excitation unit for controlling the operation of the phased array unit, gathering and processing information from the ultrasonic transducers, and generating a two-dimensional, color coded image that characterizes the integrity of the spot weld.

2. The system of claim 1, further comprises at least two sheets of material that have been joined together by resistance welding, and wherein the resistance welding has generated at least one spot weld.

3. The system of claim 1, wherein the combination of materials further includes a flexible membrane mounted on the end of the probe and a fluid filled chamber or solid sound delay material disposed between the membrane and the array.

4. The system of claim 1, wherein the transducer elements are further arranged into discrete subgroups, and wherein each subgroup may be activated independently of the other subgroups and at different time intervals.

5. The system of claim 4, wherein activating each subgroup independently of the other subgroups and at different time intervals for each element in the subgroup provides signal focusing and steering capability.

6. The system of claim 4, where in the controller is further operative to detect the surface of a spot weld for each element subgroup; adjust instrument gating to compensate for surface profile and differences in probe orientation; measure the signal amplitude ratio between responses reflected from the unbonded areas and areas with good bond: recognize a subset of the responses as being reflected from the unbonded areas associated with the spot weld and to separate the subset from a remainder of the responses: and measure the extent of the non-delamination dimensions.

7. The system of claim 1, where in the controller is a computer.

8. A non-destructive test system for characterizing a spot weld, comprising:
   (a) an acoustic probe, wherein the acoustic probe further includes:
      (i) a plurality of ultrasonic transducer elements arranged in a curved array at one end of the acoustic probe, wherein the transducer elements are operative to both generate ultrasonic signals and to receive reflections thereof; and
      (ii) a combination of materials for allowing the probe to conform to a contoured surface of the spot weld while enabling sound energy to be transferred directly into the spot weld under test conditions, wherein the combination of materials further includes a flexible membrane mounted on the end of the probe and a fluid filled chamber or solid sound delay material disposed between the membrane and the array; and
   (b) a phased array excitation unit in electrical communication with the array of transducer elements for ultrasonically exciting the transducer elements; and
   (c) a computerized controller in electrical communication with the phased array excitation unit for controlling the operation of the phased array unit, gathering and processing information from the ultrasonic transducers, and generating a two-dimensional, color coded image that characterizes the integrity of the spot weld.

9. The system of claim 8, further comprises at least two sheets of material that have been joined together by resistance welding, and wherein the resistance welding has generated at least one spot weld.

10. The system of claim 9, wherein activating each subgroup independently of the other subgroups and at different time intervals for each element in the subgroup provides signal focusing and steering capability.

11. The system of claim 9, where in the controller is further operative to detect the surface of a spot weld for each element subgroup; adjust instrument gating to compensate for surface profile and differences in probe orientation; measure the signal amplitude ratio between responses reflected from the unbonded areas and areas with good bond; recognize a subset of the responses as being reflected from the unbonded areas associated with the spot weld and to separate the subset from a remainder of the responses; and measure the extent of the non-delamination dimensions.

12. The system of claim 8, wherein the transducer elements are further arranged into discrete subgroups, and wherein each subgroup may be activated independently of the other subgroups and at different time intervals.

13. A non-destructive test system for characterizing a spot weld, comprising:
  (a) an acoustic probe, wherein the acoustic probe further includes:
    (i) a plurality of ultrasonic transducer elements arranged in a curved array at one end of the acoustic probe, wherein the transducer elements are operative to both generate ultrasonic signals and to receive reflections thereof, wherein the transducer elements are further arranged into discrete subgroups, and wherein each subgroup may be activated independently of the other subgroups; and
    (ii) a combination of materials for allowing the probe to conform to a contoured surface of the spot weld while enabling sound energy to be transferred directly into the spot weld under test conditions, wherein the combination of materials further includes a flexible membrane mounted on the end of the probe and a fluid filled chamber or solid sound delay material disposed between the membrane and the array; and
  (b) a phased array excitation unit in electrical communication with the array of transducer elements for ultrasonically exciting the transducer elements; and
  (c) a computerized controller in electrical communication with the phased array excitation unit for controlling the operation of the phased array unit, gathering and processing information from the ultrasonic transducers, and generating a two-dimensional, color coded image that characterizes the integrity of the spot weld.

14. The system of claim 13, further comprises at least two sheets of material that have been joined together by resistance welding, and wherein the resistance welding has generated at least one spot weld.

15. The system of claim 13, wherein the transducer elements are further arranged into discrete subgroups, and wherein each subgroup may be activated independently of the other subgroups and at different time intervals.

16. The system of claim 15, wherein activating each subgroup independently of the other subgroups and at different time intervals for each element in the subgroup provides signal focusing and steering capability.

17. The system of claim 15, where in the controller is further operative to detect the surface of a spot weld for each element subgroup; adjust instrument gating to compensate for surface profile and differences in probe orientation; measure the signal amplitude ratio between responses reflected from the unbonded areas and areas with good bond; recognize a subset of the responses as being reflected from the unhonded areas associated with the spot weld and to separate the subset from a remainder of the responses; and measure the extent of the non-delamination dimensions.

* * * * *